United States Patent [19]

Wolf et al.

[11] 4,209,466

[45] Jun. 24, 1980

[54] MANUFACTURE OF FORMALDEHYDE

[75] Inventors: Dieter Wolf, Gruenstadt; Hans Diem, Ludwigshafen; Otto Grabowsky, Limburgerhof; Guenther Matthias, Ludwigshafen, all of Fed. Rep. of Germany

[73] Assignee: BASF Aktiengesellschaft, Fed. Rep. of Germany

[21] Appl. No.: 486,676

[22] Filed: Jul. 8, 1974

[30] Foreign Application Priority Data

Jul. 10, 1973 [DE] Fed. Rep. of Germany ....... 2334981

[51] Int. Cl.$^2$ ............................................ C07C 45/16
[52] U.S. Cl. ................................. 568/487; 422/197
[58] Field of Search .................................. 260/603 C

[56] References Cited

U.S. PATENT DOCUMENTS

| | | | |
|---|---|---|---|
| 2,545,889 | 3/1951 | MacLean | 260/643 E |
| 2,614,072 | 10/1952 | Carlson et al. | 260/643 E |
| 3,431,082 | 3/1969 | Sellin | 23/288 M |

FOREIGN PATENT DOCUMENTS

| | | | |
|---|---|---|---|
| 218492 | 3/1961 | Austria | 260/603 HF |
| 539300 | 4/1957 | Canada | 260/603 HF |

OTHER PUBLICATIONS

Walker, Formaldehyde, Reinhold Publishing Corp., New York, pp. 16–25 and 215 (1967).
Ullmann's Encyklopaedie der Technischen Chemie, vol. 3, pp. 475–486 and vol. 9, pp. 598–599.
Fry, H. S. et al., Rec. Trav. Chim., 50, pp. 1060–1065 (1931).
Loew, O., Ber., vol. 20, 144 (1887).

*Primary Examiner*—Bernard Helfin
*Assistant Examiner*—G. T. Breitenstein
*Attorney, Agent, or Firm*—Keil & Witherspoon

[57] ABSTRACT

Manufacture of formaldehyde by oxidative dehydrogenation of methanol in the presence of a silver catalyst using methanol obtained from a condensate derived from the evaporation of aqueous reaction mixtures in the synthesis of urea resins and then treated with caustic soda solution under specific conditions of temperature, pressure, residence time and initial formaldehyde concentration. The formaldehyde obtained is a disinfectant, tanning agent, reducing agent and starting material for the manufacture of synthetic resins, adhesives and plastics.

10 Claims, No Drawings

MANUFACTURE OF FORMALDEHYDE

This application discloses and claims subject matter described in German Pat. application P 23 34 981.7, filed July 10, 1973, which is incorporated herein by reference.

This invention relates to a process for the manufacture of formaldehyde by oxidative dehydrogenation of methanol in the presence of a silver catalyst using methanol obtained from a condensate derived from the evaporation of aqueous reaction mixtures in the synthesis of urea resins and treated with caustic soda solution under specific conditions of temperature, pressure, residence time and initial formaldehyde concentration.

One of the important uses of formaldehyde is its reaction with urea to form the aminoplastics known as urea resins. Usually, the formaldehyde synthesis plants and the aminoplastics synthesis plants are located close together or may even be combined together. Information on the preparation of urea resins is given in Ullmann's Encyklopaedie der technischen Chemie, Vol. 3, pp. 475–486 and Vol. 9, pp. 598–599. Generally 30 to 40% aqueous formaldehyde solutions are used. Following the reaction, a considerable portion of the water in the reaction mixture is separated by evaporation and condensed. This process of concentrating the reaction mixture leads to evaporation not only of water but also of other volatile materials such as formaldehyde, nitrogenous compounds and the methanol entrained with the formaldehyde solution.

For many years, attempts have been made, in industry, to re-use the said condensate (obtained in the synthesis of urea resins) in the manufacture of formaldehyde. This is so for the following reasons. The methanol and formaldehyde fractions may be re-used in the synthesis of formaldehyde. However, there are serious drawbacks in using the condensate directly in the synthesis of formaldehyde. Due to impurities or catalyst poisons present in such condensates, there is frequently a very rapid rise in pressure at the catalyst and this leads to stoppages within a short time. Usually, the methanol conversion and thus the formaldehyde yield falls, resulting in an increase in the methanol content of the formaldehyde solution obtained. All of these undesirable results occur sporadically and the duration of such stoppages usually varies considerably. These drawbacks together have hitherto prevented large-scale use of condensates from urea resin synthesis in the synthesis of formaldehyde. It has not hitherto been possible to determine which of the impurities or materials in the condensate are the cause of these difficulties.

On the other hand, this condensate cannot be discarded as waste water to rivers on account of its high biological oxygen demand (BOD value), its chemical oxygen demand (COD value) and its water-polluting effect. The BOD value is defined as the amount of oxygen consumed in mg per g of substance in the biological degradation under standard conditions during 5 days, whilst the COD value is defined as the amount of oxygen consumed in mg per g of substance assuming that the substance is completely oxidized to $CO_2$, $H_2O$ and $N_2$ by oxygen. (Chemical Engineering 11, 1972, pp. 97–104).

Canadian Patent 539,300 states that methanol-containing (column 2, line 55) and formaldehyde-containing (column 3, line 1) waste waters are difficult to process in an economical manner on account of their high oxygen demand (column 2, lines 34–36). This patent thus recommends that formaldehyde-containing and methanol-containing waste waters should be purified by oxidation in the presence of a catalyst at from 100° to 350° C. and at a pressure of from 27 to 170 atmospheres. The drawback of this method is that all of the organic components of such waste waters, including the methanol, are destroyed. Furthermore, expensive apparatus and a catalyst sensitive to external influences are required (column 3, lines 51–53). German Published Application No. 1,244,144 describes a number of further processes for the treatment of waste waters and lists their drawbacks. For example, the formaldehyde may be distilled from the waste waters in vacuo or under pressure. The drawback is the high energy consumption. Furthermore, the equipment, particularly the pressure column, is expensive. Another method mentioned is to distil formaldehyde by means of entraining agents. This method, too, is uneconomical on account of the large amounts of entraining agents used. German Published Application No. 1,244,144 recommends that the formaldehyde be acetalized at 35° to 65° C. and at a pH of less than 4, the formaldehyde dimethyl acetal being distilled off and fed to the formaldehyde synthesis. This process suffers from the disadvantage that the acetalization takes place very slowly. The long reaction times call for a large reaction volume and thus involve a high outlay. The reaction is acidically catalyzed using sulfuric acid, and this causes corrosion problems.

This invention relates to a novel process for producing formaldehyde in a simpler and more economical manner by using the condensate obtained from the synthesis of urea resins without the above difficulties.

We have found that formaldehyde may be advantageously prepared by oxidative dehydrogenation of methanol in the presence of a silver catalyst and in the presence of steam at elevated temperature, provided that the reaction is carried out using methanol which has been separated from a condensate which has been obtained by evaporating aqueous reaction mixtures derived from the synthesis of urea resins and has then been treated with caustic alkali metal in a reactor over a residence time of from 8 to 25 minutes with substantially no backmixing, the initial concentration of formaldehyde being up to 5% by weight and the temperature being from 80° to 115° C. and the pressure from 2 to 20 atmospheres.

Compared with prior art processes, the process of the invention produces formaldehyde in a simpler and more economical manner and without the occurrence of the above difficulties when using the condensate obtained from the synthesis of urea resins. Using the methanol obtained from these condensates does not lead to stoppages or poorer results. The total losses of formaldehyde and methanol are reduced, since the content of formaldehyde usually falls to less than 0.01% by weight and, on the other hand, the content of methanol, which may be easily separated by subsequent distillation for example, rises from generally 0.5 to 5% by weight to 0.6 to 7.5% by weight. The formic acid formed is present in the form of sodium formate. These advantageous results are surprising, as one would have expected the conditions used in the invention and the alkaline nature of the treating agent to produce large quantities of polymer of formaldehyde, particularly hexose and other sugars.

Formaldehyde and sugars have high BOD and COD values compared with sodium formate, as shown by the following Table:

| Compound | BOD value mg of $O_2$ per g of pure substance | COD value mg of $O_2$ per g of pure substance |
| --- | --- | --- |
| formaldehyde | 900 | 1,070 |
| sodium formate | 70 | 240 |
| hexose | 600 | 1,070 |

Apart from the recovery of the methanol, there is thus the added advantage of improved disposal of the waste waters and the consequent reduction in environmental pollution problems. For example, 1% formaldehyde solutions having a BOD value of 9,000 are converted, by separation of the methanol by the process of the invention, to waste waters having a BOD value of 790, i.e. about 8.8% of the initial value.

Similarly, it would have been expected that the conditions used in the present invention and the substantial amounts of nitrogen compounds contained in the waste waters derived from urea resin synthesis would lead to poisoning of the catalyst and to a reduction in the yield of formaldehyde by the ammonia and amines distilled with the methanol. For example, Austrian Patent 218,492 states that even small amounts of impurities contacting the catalyst with the starting materials reduce the activity of the catalyst very greatly. In particular, impurities such as ammonia and amines or ammonia-containing substances reduce the life of the catalyst to a great extent. Washing with aqueous caustic soda solution merely removes the acid components. Thus the advantageous results of the process of the invention are also surprising in view of the by-products which are still present in the condensate after the treatment and which are detrimental to the synthesis of formaldehyde.

The formaldehyde synthesis may be carried out using the methanol separated from the condensate of the urea resin synthesis (methanol of the invention) either alone or, conveniently, together with a (synthetic) methanol prepared by a synthesis process advantageously in a ratio of from 0.1 to 1 part by weight of methanol of the invention to 1 part by weight of synthetic methanol.

Suitable synthetic methanols for use in the formaldehyde synthesis are pure methanol, commercial-grade methanol or, advantageously, mixtures thereof with water or condensate. The concentration of the aqueous mixtures may advantageously be from 50 to 95% by weight and preferably from 70 to 90% by weight of methanol. In an advantageous embodiment, crude methanol is used which has been purified by the process described in German Published Application No. 1,277,834 and German Patent Nos. 1,235,881 and 1,136,318 by separation of a low-boiling fraction or by treatment with oxidizing agents and/or alkalis. In general the methanol is fed to the reaction chamber in vapor form alone or in admixture with inert gas. A suitable inert gas for use in our process is, for example, nitrogen.

Suitable oxidizing agents are pure oxygen or, more conveniently, gases containing free oxygen, particularly air. Oxygen and methanol are conveniently used in a molar ratio of from 0.3 to 0.6 and in particular from 0.4 to 0.5 mole of of oxygen (in the form of air) to 1 mole of methanol.

Any silver catalysts are suitable for use in the process of the invention, for example the silver catalysts described in German Published Application 1,231,229 and Ullmann's Encyklopaedie der technischen Chemie, Vol. 7, pp. 659 et seq. We prefer to use double-layer silver catalysts, for example the catalysts described in German Published Application 1,294,360 and laid open German Patent Application 19 03 197. For information on the manufacture of the catalysts and the method of carrying out the reaction therewith, see the cited references. One preferred embodiment of the process of the invention consists in carrying out the reaction in a double-layer catalyst in which the bottom layer has a depth of from 15 to 40 mm and in particular from 20 to 30 mm and contains at least 50% by weight of crystals having a particle size of from 1 to 4 mm and in particular of from 1 to 2.5 mm, whilst the top layer has a depth of from 0.75 to 3 mm and in particular from 1 to 2 mm and contains crystals having a particle size of from 0.1 to 1 and in particular of from 0.2 to 0.75 mm, the space velocity being from 1 to 3 tons and in particular from 1.4 to 2.4 tons of methanol per square meter of catalyst bed cross-section per hour. In large-scale work, we prefer to use catalyst beds having diameters of at least 0.5 meter and preferably of from 1 to 3 meters. Where single-layer catalysts are used, the space velocity is also preferably from 1 to 3 tons and in particular from 1.4 to 2.4 tons of methanol per square meter of catalyst bed cross-section per hour. The steam present in the synthesis of formaldehyde is partly formed during the reaction. To form the other portion, water is added to the evaporator, in which advantageously water and methanol are evaporated together with the passage of air, which may either be passed into the liquid itself or into the space above the said liquid in the evaporator.

The condensate from the urea resin synthesis contains, in addition to water, usually methanol and formaldehyde, generally in amounts of from 0.4 to 5% by weight each. The said nitrogenous impurities and other impurities or catalyst poisons entrained with the condensate generally total less than 1% by weight, based on the condensate. The condensates are produced, for example, in the manufacture of mono- and di-methylol urea; urea resin molding compositions; tri- and tetra-methylol urea; thio-urea and guanidine condensates; monophenyl urea and acetylene diurea resins; resins modified with alcohols, for example alkanols of from 1 to 5 carbon atoms or benzyl alcohol; resins modified with ammonia or amines; corresponding coating resins, casting resins, glues, adhesives, resins used as core sand binders and foamed resins. Thus, according to the process used in the aminoplastics synthesis, the substances contained in the condensate may be, in addition to ammonia and amines such as methylamine, ethanolamine and diethanolamine, other substances such as biuret derivatives, formic acid, ammonium formate, ammonium carbonate, alkanols of from 1 to 5 carbon atoms, ethylene glycol and glycerol.

The condensate produced in the urea resin synthesis has a concentration of up to 5% and in general of from 0.4 to 5% and preferably of from 1 to 3% by weight of formaldehyde. This initial concentration is reduced to less than 0.01% by weight. In general, the content of formaldehyde is below the detection level. The treatment is carried out at a temperature of from 80° to 115° C. and preferably from 85° to 95° C. and under a pressure of from 2 to 20 and preferably from 2 to 10 atmospheres using caustic alkali, preferably caustic potash and, more preferably, caustic soda. Advantageously, molar amounts of from 0.8 to 2 and preferably of from 1 to 1.1 moles of alkali metal hydroxide per mole of formaldehyde are used by adding said hydroxides in the form of 10 to 50% and preferably 20 to 30% w/w aqueous solutions. Suitable treatment times (residence times in the reactor) are from 8 to 25 minutes and preferably from 10 to 15 minutes. The treatment of the condensate and the removal of the methanol are generally carried out continuously.

The treatment is carried out in a reactor with substantially avoidance of backmixing, the mixture usually being passed through the reactor continuously in plug flow. An ideal plug flow is considered to be a flow showing no longitudinal mixing, such as may be produced in a narrow reaction tube or in a cascade of a large number of stirred vessels. In plug flow, the rate of flow and the concentrations of the fluid are substantially equal at all points over the cross-section of the tube. For information on the definition of plug flow, see Grassmann "Einfuhrung in die thermische Verfahrenstechnik" (de Gruyter, Berlin, 1967), pp. 294, 299 and 308. Advantageously, the reactors used are reaction tubes having diameters of from 100 to 1,000 mm and lengths of from 2,000 to 20,000 mm and containing packing elements having a diameter of from 10 to 50 mm or reaction tubes having diameters of from 10 to 100 mm and lengths of from 2,000 to 20,000 mm and subdivided into from 8 to 30 chambers, the mixture continuously passing through these chambers one after the other. Suitable packing elements are for example Raschig rings, Intos rings, Prym rings, Pall rings, Berl saddles, Intalox saddles, Torus saddles, interpack elements, Stedman elements, Haltmeier rolls, Wilson spirals and Brunswick spirals. The plug flow may also be produced in a cascade of usually not less than 4 and advantageously of from 4 to 8 stirred vessels. Caustic liquor and condensate are mixed together continuously in the first vessel, fresh liquid being fed thereto continuously and the reaction mixture being discharged continuously to the next vessel. In each vessel there is formed a mixture having the same concentration at all points, and the flow of mixture from one vessel to the next has the form of a piston stream of homogeneous rate of flow. The residence time is taken to be the average residence time of the condensate in all of the vessels of the cascade.

Following said treatment, the methanol is removed from the mixture, generally by distillation. Any type of distilling apparatus may be used, for example sieveplate, Oldershaw, glass plate, bubblecap plate and valve-plate columns, and falling-film evaporators. Advantageously, distillation is carried out at a temperature (measured at the top plate of the column) of from 63° to 70° C. and a pressure of from 1 to 1.1 atmospheres. The distillation residue, which contains alkali metal hydroxide and sodium formate generally in an amount of from 0.2 to 2.5% by weight and small amounts of decomposition products consisting of sugars or other by-products and generally in an amount of from 0.08 to 1% by weight, based on the mixture, may be passed directly to the sewage plant for biological degradation.

The formaldehyde synthesis is otherwise carried out in known manner, for example with the production of the vapor in the evaporator occurring in any desired manner. For example, the separated methanol may be evaporated separately and the condensate vapor may then be mixed with the methanol vapor and/or with oxygen or air. In another embodiment, the separated methanol is combined with further methanol and the mixture is evaporated. Other suitable embodiments include the admixture of air either simultaneously or subsequently. In all of these embodiments, additional amounts of water, advantageously in admixture with methanol, may be used. The separated methanol may be fed to the starting mixture in the evaporator or it may be introduced into the water feed or it may be fed to the evaporator together with the methanol. In a preferred embodiment of the process, the separated methanol is mixed with further methanol and water and the mixture is evaporated with the passage of air through the liquid in the evaporator. Oxidation is also carried out in known manner, for example by passing a steam/gas mixture consisting of methanol vapor, air, steam and, optionally, inert gas in the amounts stated above and at temperatures of from about 550° to 780° C. and in particular of from 640° to 750° C. through the silver catalyst. It is advantageous to cool the reaction gases leaving the catalyst zone over a short period, for example in less than 0.2 second, to temperatures of, say, from 50° to 170° C. The cooled gas mixture is then advantageously passed to an absorption tower, in which the formaldehyde is washed out of the gas mixture with water, advantageously countercurrently. The process is generally carried out at pressures of from 0.5 to 2 atmospheres and preferably from 0.8 to 1.8 atmospheres, batchwise or, preferably, continuously.

The formaldehyde obtained in the process of the invention is a disinfectant, tanning agent, reducing agent and valuable starting material for the synthesis of synthetic resins, adhesives and plastics. For information on its use as Ullmann, Vol. 7, page 670.

In the following Examples the parts are by weight.

EXAMPLE 1

600 kg/hr of waste water coming from a urea/formaldehyde resin synthesis and containing 1% by weight of formaldehyde, 1.04% by weight of methanol, 1.3% by weight of amine-containing and urea-containing polymers and having a BOD value (5 days) of 35,500 are mixed at 90° C. with 28.3 kg of 15.6% w/w caustic soda solution, per hour, and the mixture is passed through the reactor.

The reactor consists of a refined steel tube having an internal diameter of 20 cm and a length of 5.25 meters. The reactor is packed with Raschig rings of refined steel and having a diameter of 1.5 cm. The volume of the reactor is 149 liters. The mixture is passed upwardly through said reactor.

The temperature in the reactor is 90° C. at its input end, 92° C. over the first third and again 90° C. at its output end. The pressure is adjusted to 4 atmospheres by means of a valve. The residence time is 14 minutes. On leaving the reactor, the methanol contained in the mixture (9.1 kg/hr) is continuously distilled off. The solution remaining at the base of the evaporator contains virtually no formaldehyde, no methanol, 1.3% by weight of by-products, mainly sugars, polymers and sodium formate. The BOD value is now 2,870 (8.1% of the initial value). The COD value is 3,000 (10.2% of the initial value).

3,000 tons of the methanol obtained are mixed with 7,000 tons of methanol in the form of crude methanol and 6,770 tons of water. The mixture is evaporated while 20,640 tons of air are passed through it. The resulting vapor mixture is passed, at 690° C. and 1.15 atmospheres of total pressure and a space velocity of 2.04 tons of methanol per square meter of catalyst bed cross-section per hour, through a layer of finely divided silver (grain diameter about 1 mm) and is then cooled to 150° C. and dissolved in 2,400 tons of water in a packed tower. There is obtained a mixture of 8,280 tons of formaldehyde (88.32% of theory), 12,440 tons of water, 260 tons of methanol (1.24% by weight of the total solution) and 1.5 kg of formic acid. The yield, conversion, formic acid content of the formaldehyde solution and the life of the catalyst (98 days) are the same as occur when the reaction is carried out with the use of methanol of the invention.

EXAMPLE 2

600 kg/hr of waste water obtained from the preparation of urea glue and containing 1.9% by weight of formaldehyde and 0.05% by weight of methanol in addition to 0.18% by weight of by-products and having a BOD value (5 days) of 22,600 is mixed, at 89° C., with 30 kg/hr of 14% w/w caustic soda solution and then passed through the reactor as described in Example 1. The temperature in the reactor is 89° C. at its input end, 91° C. in the middle and again 89° C. at its output end. The pressure is 9 atmospheres. The residence time is 14 minutes. Following the treatment, the methanol is distilled off (5.66 kg/hr). The distillation residue contains neither formaldehyde nor methanol. The BOD value is now 3,110 (13.8% of the initial value) and the COD value is 3,600 (15.7% of the initial value). The distilled methanol is mixed with crude methanol in a ratio of 1:3 and with water and is used for the manufacture of formaldehyde as described in Example 1. The yield and conversion and the life of the catalyst and the content of formic acid in the formaldehyde solution are similar to the values obtained in Example 1.

We claim:

1. A process for the manufacture of formaldehyde by oxidative dehydrogenation of methanol in the presence of a silver catalyst and in the presence of steam at elevated temperature, wherein the reaction is carried out using methanol which has been separated from a condensate which has been obtained by evaporating aqueous reaction mixtures derived from the synthesis of urea resins and which condensate has then been treated with caustic alkali in a reactor over a residence time of from 8 to 25 minutes with substantially no backmixing, the initial concentration in the condensate of formaldehyde, calculated as 100%, being up to 5% by weight and the temperature being from 80° to 115° C. and the pressure from 2 to 20 atmospheres, and further wherein the separation of the methanol from said condensate is done by distillation of the methanol in the caustic alkali treated condensate, the distillation residue being essentially free from formaldehyde.

2. A process as claimed in claim 1, wherein the treatment is carried out using a condensate obtained in the manufacture of urea resins and having an initial concentration of from 0.4 to 5% by weight of formaldehyde.

3. A process as claimed in claim 1, wherein the treatment is carried out using a condensate obtained in the manufacture of urea resins and having an initial concentration of from 1 to 3% by weight of formaldehyde.

4. A process as claimed in claim 1, wherein the caustic alkali treatment is carried out at a temperature of from 85° to 95° C.

5. A process as claimed in claim 1, wherein the caustic alkali treatment is carried out at a pressure of from 2 to 10 atmospheres.

6. A process as claimed in claim 1, wherein the caustic alkali treatment is carried out using from 0.8 to 2 moles of alkali metal hydroxide per mole of formaldehyde.

7. A process as claimed in claim 1, wherein the caustic alkali treatment is carried out with substantial avoidance of backmixing, the mixture being treated being passed through the reactor continuously in plug flow.

8. A process as claimed in claim 1, wherein the caustic alkali treatment is carried out using reaction tubes having diameters of from 100 to 1,000 mm and lengths of from 2,000 to 20,000 mm and containing packing elements having diameters of from 10 to 50 mm or in reaction tubes having diameters of from 10 to 100 mm and lengths of from 2,000 to 20,000 mm and subdivided into from 8 to 30 chambers, the mixture being passed continuously through these chambers one after the other.

9. A process as claimed in claim 1, wherein said condensate is an aqueous condensate containing methanol and formaldehyde in amounts of 0.4 to 5% by weight of each prior to the caustic alkali treatment, and wherein the distillation residue contains less than 0.1% by weight of formaldehyde, 0.2 to 2.5% by weight of each of said caustic alkali and sodium formate and 0.08 to 1% by weight of decomposition products consisting of sugars and other by-products.

10. A process as claimed in claim 1, wherein the distillation residue contains less than 0.01% by weight of formaldehyde, 0.2 to 2.5% by weight of each of said caustic alkali and sodium formate and 0.08 to 1% by weight of decomposition products consisting of sugars and other by-products, and the distillation residue having a BOD value and a COD value much smaller than the BOD value and COD value of said condensate prior to the treatment with caustic alkali.

* * * * *